United States Patent [19]

Mutschler et al.

[11] Patent Number: 4,943,563
[45] Date of Patent: Jul. 24, 1990

[54] 2,3,4-TRIACYLHEXOSE INSECT REPELLANTS

[75] Inventors: Martha A. Mutschler; John C. Steffens; Joseph C. Goffreda; Ward M. Lingey, all of Ithaca, N.Y.

[73] Assignee: Cornell Research Foundation, Inc., Ithaca, N.Y.

[21] Appl. No.: 252,769

[22] Filed: Oct. 3, 1988

[51] Int. Cl.$^5$ ............................................. A01N 43/00
[52] U.S. Cl. ...................................... 514/23; 514/25; 514/919
[58] Field of Search ..................... 514/23, 25, 919

[56] References Cited

U.S. PATENT DOCUMENTS 4,745,186  5/1988  Mudd et al. ......................... 514/23

FOREIGN PATENT DOCUMENTS 0021339  1/1981  European Pat. Off. ............... 514/25
0144296  9/1982  Japan ....................................... 514/25

*Primary Examiner*—Johnnie R. Brown
*Assistant Examiner*—Everett White
*Attorney, Agent, or Firm*—Bruce F. Jacobs

[57] ABSTRACT

2,3,4-Triacylhexoses and mixtures thereof have been found to repel insects from plants. The hexoses may be readily formulated into insect repellant compositions by blending them with inert carriers and then depositing the resultant compositions upon a surface to be protected from attack by the insects.

22 Claims, No Drawings

2,3,4-TRIACYLHEXOSE INSECT REPELLANTS

FIELD OF THE INVENTION

This invention relates to the use of 2,3,4-tri-O-acyl-hexopyranoses, referred to herein as 2,3,4-tri-O-acyl-hexoses or 2,3,4-tri-acylhexoses, as insect repellants, especially for plants. In addition, the present invention relates to insect repellant compositions and a method of repelling insects from a plant substrate to be protected. The 2,3,4-triacylhexoses may be utilized as either individual compounds or as in mixtures derived, for example, as the result of selective extraction and purification of the epicuticular exudate from plant parts of *Lycopersicon pennellii*, its hybrids and progeny.

BACKGROUND OF THE INVENTION

The plant species *Lycopersicon pennellii* Corr. (also known as *Solanum pennellii* Corr.) inhabits the extremely dry, lower, western slopes of the Central Peruvian Andes. This species has a rather wide geographic distribution that extends from El Horador (Depto. Piura) in northern Peru to Camana (Depto. Arequipa) in southern Peru. The autecology of these native populations is such that often the only other vegetation growing in close proximity to *Lycopersicon pennellii* plants are cacti and bromeliads.

As a plant species, *Lycopersicon pennellii* is morphologically intermediate between potato and tomato. However, since *Lycopersicon pennellii* is interfertile in controlled pollinations with the cultivated tomato, it is commonly grouped with other wild species of tomato. Yu (1972) and Rick (1973) have shown that among tomato species, *Lycopersicon pennellii* leaves have a unique and special ability to withstand desiccation. They also point out that *Lycopersicon pennellii* distinguishes itself from other Lycopersicon species, except *Lycopersicon chilense*, in its ability to withstand conditions of extreme drought.

Both native, greenhouse and field populations of certain *Lycopersicon pennellii* have oily glands that produce a sticky exudate which covers the surfaces of *Lycopersicon pennellii* leaves, stems, peduncles, calyxes and fruits. An analysis of lipids in the leaves of *Lycopersicon pennellii* by Ermakov (1980) showed that the leaves have a high lipid content. The Ermakov study further showed that the *Lycopersicon pennellii* leaf lipids contain some 15 fatty acid components, the predominant ones being saturated fatty acids, especially capric acid (C10:0). In cultivated tomato leaves, e.g., the cultivar Gruntovy Gribovsky, Ermakov states that unsaturated fatty acids, especially linolenic acid (C18:3), usually prevail.

In addition to analyzing total leaf lipids, Ermakov also analyzed lipids isolated from the glandular hairs of *Lycopersicon pennellii* leaves. His results show that the glandular hair lipids are mainly polar and that they comprise over 70 percent of the total lipids in the leaves. In comparing the glandular hair lipids with well known plant galactolipids (for which a high concentration of unsaturated fatty acids is characteristic), Ermakov points out the glandular hair lipids have a high concentration of saturated fatty acids, especially those with a relative molecular size or length of up to C14.

Physical entrapment of arthropods by the exudate from glandular hairs of various plants is well known in wild Solanum species such as *S. berthaultii, S. tarijense*, and *S. polyadenium*. The exudate of the four-lobed (type A) trichomes, when exposed to atmospheric oxygen, forms a viscous substance which accumulates on the tarsi and mouthparts of green peach aphid, *Myzus persicae* Sulzer, the potato aphid, *Macrosiphum Euphorbiae* Thomas, and the potato leafhopper, *Empoasca fabae* Harris. The viscous material hardens and effectively immobilizes the insects, resulting in their death through starvation.

*S. berthaultii* also possesses a second type of glandular trichome (type B) which is slender and continuously secretes a sticky substance at its tip. This type of trichome has been found to be important in entrapping the two-spotted spider mite, *Tetranychus urticae* Koch, and tarsonemid mites; mites are not powerful enough to rupture the membrane of the fourlobed glandular trichomes. Utilizing an electronic feeding monitor, Lapointe and Tingey (1984) demonstrated that aphid feeding on *S. berthaultii* leaves was characterized by a delay in probing, a decrease in the duration of probes, and that an overall physical removal of the type B exudate resulted in a decrease of resistance as measured by these parameters.

The most abundant of the types of glandular hairs in the genus Lycopersicon are the type IV and VI trichomes. The type VI trichome is similar in appearance to the type A trichomes on Solanum species while the type IV trichome is similar to the type B of Solanum. Physical entrapment of the carmine spider mite, *Tetranychus cinnabarinus* Boisduval, the two-spotted spider mite, *T. urticae*, and the greenhouse whitefly, *Trialeurodes vaporariorum* Westwood by type IV glandular exudate appears to be the principal component of resistance to these pests by certain Lycopersicon species (Gentile et al., 1969, 1968). Removal of the exudate with alcohol resulted in successful oviposition and normal nymphal development of the greenhouse whitefly (Gentile et al., 1968). The release of a viscous exudate upon rupture of the type VI trichomes is suggested as the basis for physical entrapment of insects in several wild tomato species.

*L. pennellii*, especially accession LA716, is resistant to several insect species, including greenhouse whitefly, carmine and two-spotted spider mites, and potato and green peach aphids. Insect resistance in *L. pennellii* is largely attributed to the type IV glandular hairs, which are not present on the foliage of *L. esculentum*. Resistance to greenhouse whitefly has been attributed to the entrapment of adults in the sticky exudate of type IV trichomes (Gentile et al., 1968). Physical entrapment of carmine and two-spotted spider mites and potato aphids in exudate of type IV trichomes was also suggested as the mode of resistance to these pests (Gentile et al. 1969, Gentile and Stoner 1968b). Clayberg (1975) observed that a periclinal chimera, consisting of the epidermis, with dense indumentum of *L. pennellii* and a "core" of *L. esculentum* origin, had levels of whitefly resistance equal to that in *L. pennellii* but a reduced level of resistance to potato aphids.

The type IV trichome of *L. pennellii*, its hybrids and progeny are slender hairs with pointed tips about 0.2 to 0.4 mm in length, standing on a large simple basal cell. The hair is glandular and it continuously secretes a droplet which is not membrane-bound. Further details of these trichomes may be found in Luckwill (1943). The exudate of the type IV trichomes of *L. pennellii*, its hybrids and progeny is composed of a complex mixture of glucose triesters of saturated straight chain and branched fatty acids (C4 to C12) (Burke et al. 1987). The most abundant fatty acids found in *L. pennellii* glucose esters include 2-methylpropanoic, 8-methylnonanoic and n-decanoic acids, with 2-methylbutanoic, 3-methylbutanoic and n-dodecanoic acids being present in relatively minor amounts. The positions of esterification have all been found to be the 2, 3 and 4 positions.

The 2,3,4-tri-O-acylhexoses of this invention are known compounds being disclosed in U.S. Ser. No. 709,550 filed Mar. 8, 1985, the disclosure of which is incorporated by reference. The hexoses are disclosed therein to be useful in cosmetic and toiletry formulations for humans, as "low calorie" fat substitutes in food, and as evaporation suppressants, antitranspirants and antidesiccants.

REFERENCE LIST

The scientific publications cited herein are listed below; each is expressly incorporated by reference.

Burke et al. (1987), "Polar epicuticular lipids of *L. Pennellii*," Phytochemistry, 26:2567–2571.

Clayberg (1975), "Insect resistance in a graft-induced periclinal chimera of tomato," Hort. Science, 10:13–15.

Ermakov, E. L. (1980), "Features of the chemical composition of the leaf lipids in *Solanum pennellii* Corr.", Byull Vses Nauchno-Issled Inst Rastenievod im N. I. Vavilova, 105:72–77.

Gentile and Stoner (1968), "Resistance in Lycopersicon and Solanum species to the potato aphid," J. Econ. Entomol., 61:1152–1154.

Gentile et al. (1968), "Resistance in Lycopersicon and Solanum to greenhouse whiteflies," J. Econ. Entomol., 61:1355–1357.

Gentile et al. (1969), "Lycopersicon and Solanum spp resistant to the carmine and two-spotted spider mite," J. Econ. Entomol., 62:834–836.

Lapointe, S. L. et al. (1984), "Feeding response of the green peach aphid (Homoptera: Aphididae) to potato glandular trichomes," J. Econ Entomol., 77:386–389.

Luckwill, L. C. (1943), The genus Lycopersicon: an historical, biological, and taxonomic survey of the wild and cultivated tomatoes. Aberdeen Univ. Studies No. 120, Aberdeen Univ. Press.

Rick, C. M. (1973), "Potential genetic resources in tomato species: Clues from observation in native habitats," In AM Srb, ed., Handbook of Genetics.

Yu, A. T. T. (1972), "The genetics and physiology of water usage in *Solanum pennellii* Corr. and its hybrids with *Lycopersicon esculentum* Mill," Ph. D. Thesis, Univ. Calif., Davis.

SUMMARY OF THE INVENTION

The present invention provides in one embodiment an insect repellant composition for use, especially on plants, wherein the active ingredient is a 2,3,4-tri-O-acyl D- and/or L-hexose having the structure:

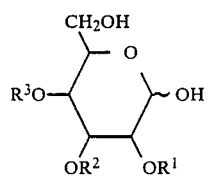

wherein the hexose is selected from the group consisting of glucose, mannose, galactose, allose, altrose, gulose, idose, and talose;

the anomeric (C-1) substituent is either alpha or beta; and $R^1$, $R^2$, and $R^3$ are each acyl groups derived from fatty acids containing about three to about thirty carbon atoms and are either straight chains or branched.

In another embodiment, the present invention provides for a method of protecting a plant from attack by insects by applying to said plant an amount of the hexose compound which is insufficient to trap or capture an adult insect but which amount is sufficient to cause the insect to not damage the plant by feeding thereon.

In a still further embodiment, the present invention provides for an insect repellant composition and a method of repelling insects from a plant wherein the active ingredient is a mixture of triacylhexoses produced from the type IV trichomes of the *Lycopersicon pennellii* plant, its hybrids and progeny.

DETAILED DESCRIPTION OF THE INVENTION

The 2,3,4-tri-O-acylhexoses which form the basis of the present invention are those having the structure:

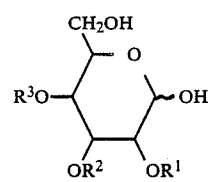

wherein the hexose is selected from the group composed of glucose, mannose, galactose, allose, altrose, gulose, idose, and talose;

the anomeric (C-1) substituent is alpha or beta; and $R^1$, $R^2$ and $R^3$ are each acyl groups derived from straight chain or branched fatty acids having about three to thirty carbon atoms.

Preferably the hexose is glucose. Also, preferably the acyl groups each contain about four to twenty carbon atoms. Most preferably, $R^1$, $R^2$ and $R^3$ are the same are derived from fatty acids selected from the group consisting of 2-methylpropanoic acid, 3-methylbutanoic acid, 2-methylbutanoic acid, 8-methylnonanoic acid and n-decanoic acid.

Mixtures of 2,3,4-tri-O-acylhexoses, in varying proportions, may be used. Preferably the mixtures will be derived as the result of selective extraction and purification of the epicuticular exudate from type IV trichomes from plant parts of *Lycopersicon pennellii*, its hybrids and progeny. A typical total extract (TE) mixture has been found to contain approximately 5%–10% alkanes and approximately 1% terpenoids. A typical distribution of fatty acid components in a glucolipid (G) mixture (comprised essentially of hexose sugar components and fatty acid components, wherein the hexose sugar components of the mixture are glucose molecules) is about 41% 2-methylpropanoic acid, about 4.5% 2-methylbutanoic acid, about 4% 3-methylbutanoic acid, about 31.5% 8-methylnonanoic acid, and about 10.5% decanoic acid. At room temperature this purified "glucolipid mixture" is a colorless, odorless, oil liquid.

The 2,3,4,-tri-O-acylhexoses of the present invention may also be synthesized chemically by known methods. For example, to incorporate three identical acyl groups at the 2, 3, and 4 positions on the hexose moiety, the following method may be used. One molar equivalent of hexose is mixed with two molar equivalents of trityl chloride in dry pyridine. The resulting mixture is shaken vigorously, then stirred for several days. A suspension of this mixture is mixed with three molar equivalents of acyl chloride in chloroform. After standing overnight, the mixture is diluted with cold, 2% aqueous bicarbonate, extracted with chloroform, dried over anhydrous sodium sulfate and purified by preparative thin layer chromatography in acetone/hexane (1:5) to yield 1,6-di-O-trityl-2,3,4-tri-O-acylhexoses. The blocking group is removed, e.g., by stirring overnight with $PtO_2$ in an atmosphere of hydrogen, filtration, partial removal of the solvent in vacuo, and partitioning between hexane and $MeOH/H_2O$ (75:25). When desired the product may be further purified by reverse phase preparative TLC in $MeOH/H_2$ (70:30).

Hexoses containing mixed acyl substituents may also be synthesized easily using known chemical methods. Thus, for example, readily available 4,6-benzylidene-alpha-1-O-methyl-hexose may be acylated with one equivalent of acyl chloride ($R^1Cl$) in dry chloroform and pyridine, followed by the addition of a second equivalent of acyl chloride ($R^2Cl$) to give 2,3-di-O-acyl-4,6-benzylidenealpha-methyl-hexose. After removal of the benzylidene moiety with hydrogen over platinum, the 6-hydroxyl can be reprotected with a slight molar excess of trityl chloride in pyridine. This product can be acylated with one equivalent of a third acyl chloride and deprotected, e.g. by hydrogenation over platinum, to give 2,3,4-tri-O-acylalpha-methylhexose, where the acyl groups have been specifically selected. The methyl group can be removed by mild hydrolysis.

Detailed methods for synthesizing the 2,3,4-tri-O-acylhexoses of the present invention are outlined in the examples of U.S. Ser. No. 709,550, filed Mar. 8, 1985, and incorporated herein by reference.

The 2,3,4-tri-O-acylhexoses are suitable for repelling insects from plant surfaces which are coated with the acylhexoses. They are particularly suitable for preventing damage to plants by planteating insects. Examples of insects which are repelled by the acylhexoses include those of the orders: Acarina, Coleoptera, Diptera, Homoptera, Lepidoptera, Thysanoptera, and the like. Thus, insects which are protected against include those belonging to families including Agromyzidae, Aleyrodidae, Aphididae, Chrysomelidae, Cicadellidae, Gelechiidae, Meloidae, Noctuidae, Pseudococcidae, Sphingidae, Tarsonemidae, Tetranychidae, and Thripidae. In particular, the compounds of the present invention provide protection to plants from numerous specific insects such as: tarsonemid mites, carmine spider mites, two spotted spider mites, leaf beetles, blister beetles, potato flea beetles, tomato flea beetles, flea beetles, tobacco flea beetles, Colorado potato beetles, leafminer flies, cowpea aphids, bean aphids, melon aphids, buckthorn aphids, foxglove aphids, aphids, potato leafhoppers, potato aphids, aster leafhoppers, green peach aphids, citrus mealybugs, greenhouse whiteflies, American bollworms, cotton budworms, cotton bollworms, tomato pinworms, tobacco hornworms, variegated cutworms, potato tubermoths, beet armyworms, fall armyworms, armyworms, thrips, onion thrips, and the like.

The plants which are protected from such insects are those which, in the absence of the acylhexoses, would otherwise be subject to damage by the insects eating thereon. Such plants include both ornamental plants and productive plants. Examples of such ornamental plants include: roses, chysanthemums, carnations, poinsettias, impatiens, and a wide range of other trees, shrubs, and herbaceous annuals. Examples of such productive plants include: corn, soybean, sunflower, tomato, tobacco, potato, wheat, oats, alfalfa, and other crop plants. In general, because the host range of insects which are repelled by the acylhexoses is extremely broad, the range of plants which are protected thereby is equally as broad.

The 2,3,4-tri-O-acylhexoses may be used either alone or more preferably together with inert carriers customarily employed in conventional formulation practice, and may thus be processed in known manners, for example, into the form of emulsion concentrates, directly sprayable or dilutable solutions, diluted emulsions, wettable powders, soluble powders, dusts or granulates, and also encapsulations or microencapsulations in, for example, polymeric substances. The processes used to apply the insect repellants, such as spraying, atomizing, dusting, scattering or pouring and likewise the specific form of composition, are selected based upon the objectives to be achieved and the given conditions.

The insect repellant compositions, i.e. the compositions or preparations containing the 2,3,4-tri-O-acylhexose and preferably a solid or liquid carrier additive are produced in a known manner. For example, intimate mixing and/or grinding of the active ingredients with extenders, such as with solvents, solid carriers, and optionally surface-active compounds.

Suitable solvents include: aromatic hydrocarbons, preferably the fractions $C_8$ to $C_{12}$, such as xylene mixtures or substituted naphthalenes, aliphatic hydrocarbons, such as cyclohexane or paraffins, alcohols and glycols, as well as ethers thereof, such as ethanol, ethylene glycol, ethylene glycol monomethyl or ethyl ethers, ketones such as cyclohexanone, strongly polar solvents, such as N-methyl-2-pyrrolidone, dimethyl sulfoxide or dimethylformamide, as well as optionally expoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Depending on the nature of the active ingredients to be formulated, suitable surface-active compounds are: nonionic, cationic and/or anionic compounds having good emulsifying, dispersing and wetting properties.

The insect repellant compositions will generally contain about 0.1 to about 99.9 percent by weight of a 2,3,4-tri-O-acylhexose or a mixture of 2,3,4-tri-O-acylhexoses with the balance of the composition being a solid or liquid carrier to assist in the delivery of the active ingredient onto the plant surfaces to be protected.

Whereas commercial products are preferably in the form of concentrated compositions, the preparations employed by the end-user will have, as a rule, a considerably lower concentration of active ingredient.

The compositions can also contain further additives, such as stabilizers, antifoaming agents, viscosity regulators, binders and adhesives, as well as fertilizers or other active ingredients for obtaining special effects.

FORMULATION EXAMPLES FOR LIQUID ACTIVE INGREDIENTS (%=PERCENT BY WEIGHT)

| 1. Emulsion concentrates | (a) | (b) | (c) |
|---|---|---|---|
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the required concentration can be produced from these concentrates by dilution with methanol.

| 2. Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in isopropanol, the solution is sprayed onto the carrier, and the solvent is then evaporated off in vacuo

| 3. Dusts | (a) | (b) |
|---|---|---|
| active ingredient | 2% | 5% |
| highly dispersed silicic acid | 1% | 5% |
| talcum | 97% | — |
| kaolin | — | 90% |

Dusts ready for use are obtained by the intimate mixture together of the carriers with the active ingredient.

FORMULATION EXAMPLES FOR SOLID ACTIVE INGREDIENTS (%=PERCENT BY WEIGHT)

| 4. Wettable powders | (a) | (b) | (c) |
|---|---|---|---|
| active ingredient | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with additives and the mixture is thoroughly ground in a suitable mill. The wettable powders which are obtained may be diluted with water to give suspensions of the required concentrations.

| 5. Emulsion concentrate | |
|---|---|
| active ingredient | 10% |
| octylphenol polyethylene glycol ether (4-5 mols of ethylene oxide) | 3% |
| castor oil polyglycol ether | 3% |
| | 4% |

| 5. Emulsion concentrate -continued | |
|---|---|
| (36 mols of ethylene oxide) | |
| cyclohexanone | 30% |
| xylene mixture | 50% |

Emulsions of the concentrate required can be obtained from this concentrate by dilution with water.

| 6. Dusts | (a) | (b) |
|---|---|---|
| active ingredient | 5% | 8% |
| talcum | 95% | — |
| kaolin | — | 92% |

Dusts ready for use are obtained by mixing the active ingredient with the carriers, and grinding the mixture in a suitable mill.

| 7. Extruded granulate | |
|---|---|
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded, granulated and then dried in a stream of air.

| 8. Coated granulate | |
|---|---|
| active ingredient | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in like manner.

| 9. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

The acylhexose insect repellants will normally be deposited upon the substrate to be protected in an amount which is substantially less than that which would physically entrap the insect on the surface of the substrate. The normal concentration of acylhexoses on L. pennellii itself is around 300 ug/cm$^2$. Insect repellancy has been observed at acylhexose concentrations as low as 25 ug/cm$^2$ and complete avoidance of a treated leaf at concentrations of about 100 to 150 ug/cm$^2$. In actual use the specific concentration to be used will be determined by routine tests of the specific plant to be protected from a specific insect or group of insects which are expected to come in contact with that plant.

Having generally described the invention, a more complete understanding can be obtained by reference to the following specific examples which are included for purposes of illustration only and are not intended to be limiting unless otherwise specified. All parts and percents are by weight unless otherwise specified.

EXAMPLE I

This example illustrates the effectiveness of the exudate of type IV trichomes of *Lycopersicon pennellii* in repelling insects from plants which would otherwise be attacked by the insects.

Approximately 200 sq. cm. of leaflets of *Lycopersicon pennellii* (LA716) was dipped into two 15 ml. volumes of methanol to remove the type IV trichome exudate. Microscopic examination of treated leaves revealed that the methanolic dips were effective in removing type IV trichome exudate while not damaging the membrane-enclosed droplets of type VI trichomes. The rinsates were combined and then diluted with additional methanol so that 10 ul represented one-half the exudate obtained from 1 sq. cm. of leaf surface. Gas chromatographic analysis of the rinsate as well as thin layer chromatography confirmed that the rinsate contained a mixture of 2,3,4-tri-O-acylglucoses wherein the esters are predominately of short to medium chain length, i.e. $C_4$ to $C_{12}$.

To evaluate the effectiveness of this mixture of 2,3,4-tri-O-acylhexoses at preventing an insect from feeding upon a plant leaf, an artificial leaf was created according to the teaching of Ave et al. (Phenolic constituents of glandular trichomes on *Solanum berthaultii* and *S. polyadenium*, Amer. Potato J., 63:473–480, 1986) by enclosing a 20 weight percent sucrose solution within Parafilm.

Two feeding ports were provided, each having an area of 1 sq. cm. To insure even coverage of the acylhexose mixture on the Parafilm, 2.5 ul of a solution of the glucose esters was dissolved in a mixture of acetone, chloroform, and paraffin oil (15:3:1) and was uniformly applied onto the feeding membrane surface.

Replicated tests of a choice assay (wherein one feeding port is covered with solvents only while the other includes the acylhexose or mixture of acylhexoses) showed a significant avoidance of the feeding area treated with the 2,3,4-tri-O-acylglucose mixture when potato aphids (*Macrosiphum euphorbiae*) were placed within the nylon gauze and allowed to feed on the enclosed sucrose solution. There was significant reduction in feeding when the acylglucose mixture was used in an amount as low as 25 ug/cm². There was complete avoidance of the test port at concentrations of 150 ug/cm² and higher.

Replicated tests of a no-choice assay (wherein both feeding ports are covered with the acylglucose mixture) demonstrated that between 50 to 100 ug/cm² of the acylglucose mixture was required to provide a deterrent response after only 24 hours. In long term no choice assays there was significantly higher mortality in chambers treated with 100 ug/cm² than in control chambers after 48 and 72 hours, apparantly because the aphids preferred to starve to death rather than settle and feed on the acylhexose-coated areas.

EXAMPLE II

The procedure of Example I is repeated using some individual glucose esters from *L. pennellii* rather than the complete mixture as in Example I. In the specific esters evaluated, the R groups are as follows:
a: triisobutyric
b: diisobutyric, monoisovaleric
c: monoisobutyric, diisovaleric
d: diisobutyric, monoisocapric
e: monoisobutyric, monoisovaleric, monoisocapric
f: diisolvaleric, monoisocapric
g: monoisobutyric, diisocapric
h: monoisovaleric, diisocapric
i: triisocapric.

The results of the feeding tests show no significant difference in performance between the mixture of glucose esters used in Example I and the individual esters utilized herein. Likewise, deviations in the frequency distributions among the different fractions having different chain length esters were not found to be significant.

COMPARATIVE EXAMPLE A

The procedure of Example I is repeated upon two different leaflets—the first being *L. esculentum* and the second the $F_1$ of *L. pennellii* and *L. esculentum*.

The trichome extract of *L. esculentum* contains no 2,3,4-tri-O-acylhexoses and was found to have no effect upon the feeding behavior of the aphids.

The trichome extract of the $F_1$ was found to contain the acylhexoses and was as effective as the *L. pennellii* exudate of equal concentration.

EXAMPLE III

The procedure of Example I is repeated except that the aphids are replaced by each of the following insects:
a: tarsonemid mites
b: carmine spider mites
c: two spotted spider mites
d: leaf beetles
e: tobacco flea beetles
f: Colorado potato beetles
g: leafminer flies
h: aster leafhoppers
i: citrus mealybugs
j: greenhouse whiteflies
k: potato tubermoths
l: beet armyworms.

In each case insect repellency is observed when one or both feeding ports are coated with a thin layer of the trichome extract of *L. pennellii*, though the amounts required for total avoidance varied.

EXAMPLE IV

The procedure of Example I is repeated except that 200 ug/cm² of mixed *L. pennellii* acylglucose esters was applied to the side of the Parafilm that faced away from the insect chamber to eliminate contact of the insects' feet and/or antenna with the esters while still allowing stylet contact during probing. No significant avoidance of the treated areas was observed.

EXAMPLE V

To assess the insect repellency activity of certain of the compounds of the present invention, the following compounds are prepared in accordance with the literature and tested as per Example I:

| | Chain Length of Acyl Groups | | | |
|---|---|---|---|---|
| Hexose | $R^1$ | $R^2$ | $R^3$ | D/L |
| Glucose | 4 | 5 | 5 | D |
| Glucose | 12 | 12 | 12 | L |
| Mannose | 7 | 7 | 7 | D |
| Galactose | 3 | 8 | 15 | L |
| Allose | 12 | 8 | 12 | L |
| Altrose | 18 | 18 | 4 | D |
| Gulose | 22 | 22 | 22 | L |
| Idose | 10 | 10 | 10 | L |
| Talose | 4 | 4 | 4 | D |

In each case insect repellency is observed.

EXAMPLE VI

The procedure of Example I is repeated except that the trichome extract is used as a simple dilute methanol solution. Substantially similar results occur.

EXAMPLE VII

The procedure of Example I is repeated except that the purified mixture of 2,3,4-tri-O-acylglucose esters are used to form a dust by intimately blending 2 parts of the esters, 1 part silicic acid, and 97 parts talcum to form a uniform coating. The coating is dusted on a horizontal feeding port at a rate of 100 ug active ingredients/sq. cm. The aphids again prefer to starve to death rather than feed through the esters.

What is claimed is:

1. A method of repelling insects from the surfaces of a plant which comprises applying thereto an insect repellent amount of a 2,3,4-tri-O-acylhexose of the formula:

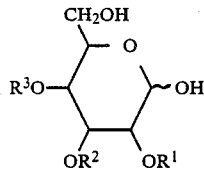

wherein the hexose is a hexose selected from the group composed of glucose, mannose, galactose, allose, altrose, gulose, idose, and talose;
the anomeric (C-1) substituent is either alpha or beta; and
$R^1$, $R^2$, and $R^3$ are each acyl groups derived from fatty acids containing from about 3 to about 30 carbon atoms;
in combination with an inert solid or liquid carrier.

2. The method of claim 1 wherein $R^1$, $R^2$, and $R^3$ are the same.

3. The method of claim 1 wherein one of $R^1$, $R^2$, and $R^3$ is different from the others.

4. The method of claim 1 wherein an R group is branched.

5. The method of claim 1 wherein the hexose is glucose.

6. The method of claim 1 wherein each of the R groups contain from about 4 to about 20 carbon atoms.

7. The method of claim 1 wherein the R groups are derived from a fatty acid selected from the group consisting of 2-methylpropanoic acid, 3-methylbutanoic acid, 2-methylbutanoic acid, 8-methylnonanoic acid, and n-decanoic acid.

8. The method of claim 1 wherein there is a mixture of different acylhexoses present.

9. The method of claim 8 wherein the mixture is derived from an epicuticular exudate from the type IV trichomes of *Lycopersicon pennellii*, its hybrids and progeny.

10. The method of claim 9 wherein the exudate is obtained by an alcohol treatment.

11. The method of claim 10 wherein the alcohol is methanol or ethanol.

12. The method of claim 1 wherein the carrier is a liquid.

13. The method of claim 12 wherein the liquid comprises an alcohol.

14. The method of claim 1 wherein the insects being repelled are selected from insects belonging to an order selected from Acarina, Coleoptera, Diptera, Homoptera, Lepidoptera, and Thysanoptera.

15. The method of claim 1 wherein the plants being treated are selected from ornamental plants and productive plants.

16. The method of claim 15 wherein the plants are productive plants selected from the group consisting of corn, soybean, sunflower, tomato, tobacco, potato, wheat, oats, alfalfa, and other crop plants.

17. A method of deterring an insect from feeding on a plant which comprises treating the surfaces of the plant with a feeding deterrant amount of a 2,3,4-tri-O-acylhexose of the formula

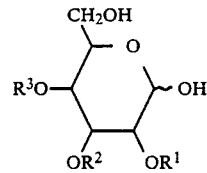

wherein the hexose is a hexose selected from the group composed of glucose, mannose, galactose, allose, altrose, gulose, idose, and talose;
the anomeric (C-1) substituent is either alpha or beta; and
$R^1$, $R^2$, and $R^3$ are each acyl groups derived from fatty acids containing from about 3 to about 30 carbon atoms.

18. The method of claim 17 wherein the 2,3,4-tri-O-acylhexose is blended with an inert liquid or solid carrier.

19. The method of claim 17 wherein the insect is selected from the group consisting of tarsonemid mites, carmine spider mites, two spotted spider mites, leaf beetles, blister beetles, potato flea beetles, tomato flea beetles, flea beetles, tobacco flea beetles, Colorado potato beetles, leafminer flies, cowpea aphids, bean aphids, melon aphids, buckthorn aphids, foxglove aphids, aphids, potato leafhoppers, potato aphids, aster leafhoppers, green peach aphids, citrus mealybugs, greenhouse whiteflies, American bollworms, cotton budworms, cotton bollworms, tomato pinworms, tobacco hornworms, variegated cutworms, potato tubermoths, beet armyworms, fall armyworms, armyworms, thrips, and onion thrips.

20. The method of claim 17 wherein the plant is selected from the group consisting of ornamental plants selected from roses, chysanthemums, carnations, poinsettias, and impatiens, and productive plants selected from corn, soybean, sunflower, tomato, tobacco, potato, wheat, oats, alfalfa, and other crop plants.

21. The method of claim 17 wherein the acylhexose is a mixture of acylhexoses.

22. The method of claim 17 wherein the acylhexose is derived from an epicuticular exudate from the type IV trichomes of *Lycopersicon pennellii*, its hybrids and progeny.

* * * * *